(12) United States Patent
Prakash

(10) Patent No.: US 9,023,026 B2
(45) Date of Patent: *May 5, 2015

(54) ARTICULATING ABLATION DEVICE AND METHOD

(71) Applicant: Vivant Medical, Inc., Boulder, CO (US)

(72) Inventor: Mani N. Prakash, Boulder, CO (US)

(73) Assignee: Covidien LP, Mansfield, MA (US)

( * ) Notice: Subject to any disclaimer, the term of this patent is extended or adjusted under 35 U.S.C. 154(b) by 83 days.

This patent is subject to a terminal disclaimer.

(21) Appl. No.: 13/740,754

(22) Filed: Jan. 14, 2013

(65) Prior Publication Data
US 2013/0131670 A1 May 23, 2013

Related U.S. Application Data

(63) Continuation of application No. 12/353,623, filed on Jan. 14, 2009, now Pat. No. 8,353,902.

(60) Provisional application No. 61/025,206, filed on Jan. 31, 2008.

(51) Int. Cl.
| A61B 18/18 | (2006.01) |
| A61B 17/70 | (2006.01) |
| A61B 18/14 | (2006.01) |
| A61B 17/00 | (2006.01) |

(52) U.S. Cl.
CPC ......... *A61B 18/1482* (2013.01); *A61B 18/1477* (2013.01); *A61B 18/149* (2013.01); *A61B 18/1492* (2013.01); *A61B 18/18* (2013.01); *A61B 18/1815* (2013.01); *A61B 2017/003* (2013.01); *A61B 2018/1425* (2013.01)

(58) Field of Classification Search
USPC .......................... 606/27–34, 41–42, 78, 261
See application file for complete search history.

(56) References Cited

U.S. PATENT DOCUMENTS

| D223,367 S | 4/1972 | Kountz |
| D263,020 S | 2/1982 | Rau, III |
| D266,842 S | 11/1982 | Villers et al. |

(Continued)

FOREIGN PATENT DOCUMENTS

| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Rebecca E Eisenberg

(57) ABSTRACT

An ablation device including a handle portion, a shaft and at least one cable. The shaft extends distally from the handle portion and includes an inner conductor and an outer conductor that substantially surrounds at least a portion of the inner conductor. The cable extends from the handle portion along at least a portion of the shaft. The distal tip of the inner conductor is positionable distally beyond a distal-most end of the outer conductor. In response to movement of the at least one cable relative to the handle portion, the distal tip of the outer conductor is movable form a first position where the distal tip is substantially aligned with a longitudinal axis defined by the outer conductor to at least a second position where the distal tip is disposed at an angle relative to the longitudinal axis.

14 Claims, 4 Drawing Sheets

(56) References Cited

U.S. PATENT DOCUMENTS

| | | | |
|---|---|---|---|
| D278,306 S | 4/1985 | McIntosh | |
| D295,893 S | 5/1988 | Sharkany et al. | |
| D295,894 S | 5/1988 | Sharkany et al. | |
| D354,218 S | 1/1995 | Van de Peer | |
| 5,893,863 A | 4/1999 | Yoon | |
| 6,052,607 A | 4/2000 | Edwards et al. | |
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,587,731 B1 | 7/2003 | Ingle et al. | |
| D487,039 S | 2/2004 | Webster et al. | |
| 6,752,767 B2 | 6/2004 | Turovskiy et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| 7,377,906 B2* | 5/2008 | Selkee | 604/95.04 |
| D576,932 S | 9/2008 | Strehler | |
| 7,468,042 B2 | 12/2008 | Turovskiy et al. | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,846,108 B2 | 12/2010 | Turovskiy et al. | |
| D634,010 S | 3/2011 | DeCarlo | |
| 8,068,921 B2 | 11/2011 | Prakash et al. | |
| 8,313,486 B2 | 11/2012 | Kim et al. | |
| 8,353,902 B2 | 1/2013 | Prakash | |
| 2003/0195499 A1 | 10/2003 | Prakash et al. | |
| 2007/0049922 A1 | 3/2007 | Rontal | |
| 2007/0203480 A1* | 8/2007 | Mody et al. | 606/33 |
| 2009/0149850 A1 | 6/2009 | Turovskiy et al. | |
| 2009/0198227 A1 | 8/2009 | Prakash | |
| 2011/0270240 A1 | 11/2011 | Shiu et al. | |
| 2012/0041433 A1 | 2/2012 | Prakash et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 90 06 694 U1 | 8/1990 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 1186274 A | 3/2002 |
| EP | 0 648 515 | 4/2003 |
| EP | 1 870 052 A2 | 12/2007 |
| EP | 1 905 375 | 4/2008 |
| EP | 2 322 111 A1 | 5/2011 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 6-292728 A | 10/1994 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2003111770 A | 4/2003 |
| JP | 2003531667 A | 10/2003 |
| JP | 2005534352 A | 11/2005 |
| JP | 2008142467 | 6/2008 |
| SU | 166452 | 11/1964 |
| SU | 401367 | 11/1974 |
| SU | 727201 | 4/1980 |
| WO | 94/04220 A1 | 3/1994 |
| WO | WO00/36985 | 6/2000 |
| WO | 01/82814 A2 | 11/2001 |
| WO | WO2010/035831 | 4/2010 |

OTHER PUBLICATIONS

U.S. Appl. No. 08/483,742, filed Jun. 7, 1995, Roger A. Stern.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid Jr.
U.S. Appl. No. 13/343,798, filed Jan. 5, 2012, William O. Reid Jr.

(56) References Cited

OTHER PUBLICATIONS

U.S. Appl. No. 13/344,753, filed Jan. 6, 2012, Lee et al.
U.S. Appl. No. 13/344,790, filed Jan. 6, 2012, Lee et al.
U.S. Appl. No. 13/358,129, filed Jan. 25, 2012, Brannan.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/657,270, filed Oct. 22, 2012, Brannan.
U.S. Appl. No. 13/657,609, filed Oct. 22, 2012, Prakash.
U.S. Appl. No. 13/657,638, filed Oct. 22, 2012, Brannan.
U.S. Appl. No. 13/681,741, filed Nov. 20, 2012, Steven Kim.
U.S. Appl. No. 13/711,067, filed Dec. 11, 2012, Brannan.
U.S. Appl. No. 13/711,086, filed Dec. 11, 2012, Brannan.
U.S. Appl. No. 13/711,164, filed Dec. 11, 2012, Brannan.
U.S. Appl. No. 13/734,638, filed Jan. 4, 2013, Bonn.
U.S. Appl. No. 13/740,706, filed Jan. 14, 2013, Rossetto.
U.S. Appl. No. 13/740,754, filed Jan. 14, 2013, Prakash.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984 ), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite• Element Codes to Model Electrical Heating and Non• Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).

(56) References Cited

OTHER PUBLICATIONS

Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. 1, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (1 PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report, corresponding to European Application No. 09151736.7, dated Jun. 12, 2009; 7 pages.

* cited by examiner

ARTICULATING ABLATION DEVICE AND METHOD

CROSS-REFERENCE TO RELATED APPLICATIONS

The present application is a continuation application, which claims priority to, and the benefit of, U.S. patent application Ser. No. 12/353,623, filed on Jan. 14, 2009, which claims the benefit of and priority to U.S. Provisional Application Ser. No. 61/025,206 entitled "ARTICULATING ABLATION DEVICE AND METHOD" filed Jan. 31, 2008 by Mani N. Prakash, the disclosures of which are herein incorporated by reference in their entireties.

BACKGROUND

1. Technical Field

The present disclosure relates to ablation devices and methods. More particularly, the disclosure relates to antennas that are insertable into tissue and capable of being articulated and that are useful for laparoscopic and endoscopic procedures.

2. Background Of Related Art

In the treatment of diseases, such as cancer, certain types of cancer cells have been found to denature at elevated temperatures that are slightly lower than temperatures normally injurious to healthy cells. These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great amount of control. This is partly why a more direct and precise method of applying microwave radiation has been sought.

Presently, there are several types of microwave probes in use, e.g., monopole, dipole, and helical. One type is a monopole antenna probe consisting of a single, elongated microwave conductor exposed at the end of the probe. The probe is sometimes surrounded by a dielectric sleeve. The second type of microwave probe commonly used is a dipole antenna consisting of a coaxial construction having an inner conductor and an outer conductor with a dielectric separating a portion of the inner conductor and a portion of the outer conductor. In the monopole and dipole antenna probe, microwave energy generally radiates perpendicularly from the axis of the conductor.

Because of the perpendicular pattern of energy radiation, conventional antenna probes are typically designed to be inserted directly into the tissue, e.g., a tumor, to be radiated. However, such typical antenna probes commonly fail to provide uniform heating axially and/or radially about the effective length of the probe.

It is often difficult to assess the extent to which the energy will radiate into the surrounding tissue, i.e., it is difficult to determine the area or volume of surrounding tissue that will be ablated. Furthermore, when conventional antennas are inserted directly into the tissue, e.g., cancerous tissue, there is a danger of dragging or pulling cancerous cells along the antenna body into other parts of the body during insertion, placement, or removal of the antenna probe.

One conventional method for inserting and/or localizing wires or guides includes a wire guide that is delivered into breast tissue, for example, through a tubular introducer needle. When deployed, the wire guide cuts into and scribes a helical path about the tissue distal to a lesion while the remainder of the distal portion of the wire guide follows the path scribed by the distal tip and locks about the tissue.

SUMMARY

The present disclosure relates to an ablation device including a handle portion, a shaft and at least one cable. The shaft extends distally from the handle portion and includes an inner conductor and an outer conductor that substantially surrounds at least a portion of the inner conductor. The cable extends from the handle portion along at least a portion of the shaft. The distal tip of the inner conductor is positionable distally beyond a distal-most end of the outer conductor. In response to movement of the at least one cable relative to the handle portion, the distal tip of the outer conductor is movable form a first position where the distal tip is substantially aligned with a longitudinal axis defined by the outer conductor to at least a second position where the distal tip is disposed at an angle relative to the longitudinal axis.

The present disclosure also relates to a method of treating tissue. The method includes providing an ablation device. The ablation device includes an antenna and at least one cable. A proximal portion of the antenna defines a longitudinal axis. The at least one cable extends along a portion of the antenna. The method also includes moving the at least one cable such that a distal tip of the antenna moves from a first position where the distal tip is substantially aligned with the longitudinal axis to at least a second position where the distal tip is disposed at an angle to the longitudinal axis.

The present disclosure also relates to an ablation system for ablating tissue. The ablation system includes an ablation device including a handle portion defining a longitudinal axis and an antenna extending distally from the handle portion. An intermediate portion of the antenna is movable from a first position where a distal tip of the antenna is substantially aligned with the longitudinal axis to at least a second position where the distal tip of the antenna is disposed at an angle to the longitudinal axis.

The present disclosure also relates to an energy applicator including a handle portion, a shaft, an electrode, and at least one cable. The shaft extends distally from the handle portion and defines a longitudinal axis. The electrode is disposed in electro-mechanical cooperation with the handle portion and is translatable with respect to the shaft. The at least one cable extends between the handle portion and the electrode. At least a portion of the electrode is positionable distally beyond a distal-most end of the shaft. In response to movement of the at least one cable relative to the handle portion, a portion of the electrode is movable from a first position where the electrode is substantially aligned with the longitudinal axis to at least a second position where at least a portion of the electrode is disposed at an angle relative to the longitudinal axis.

DESCRIPTION OF THE DRAWINGS

Embodiments of the presently disclosed ablation devices are disclosed herein with reference to the drawings, wherein.

DETAILED DESCRIPTION OF EMBODIMENTS

Figure 1:
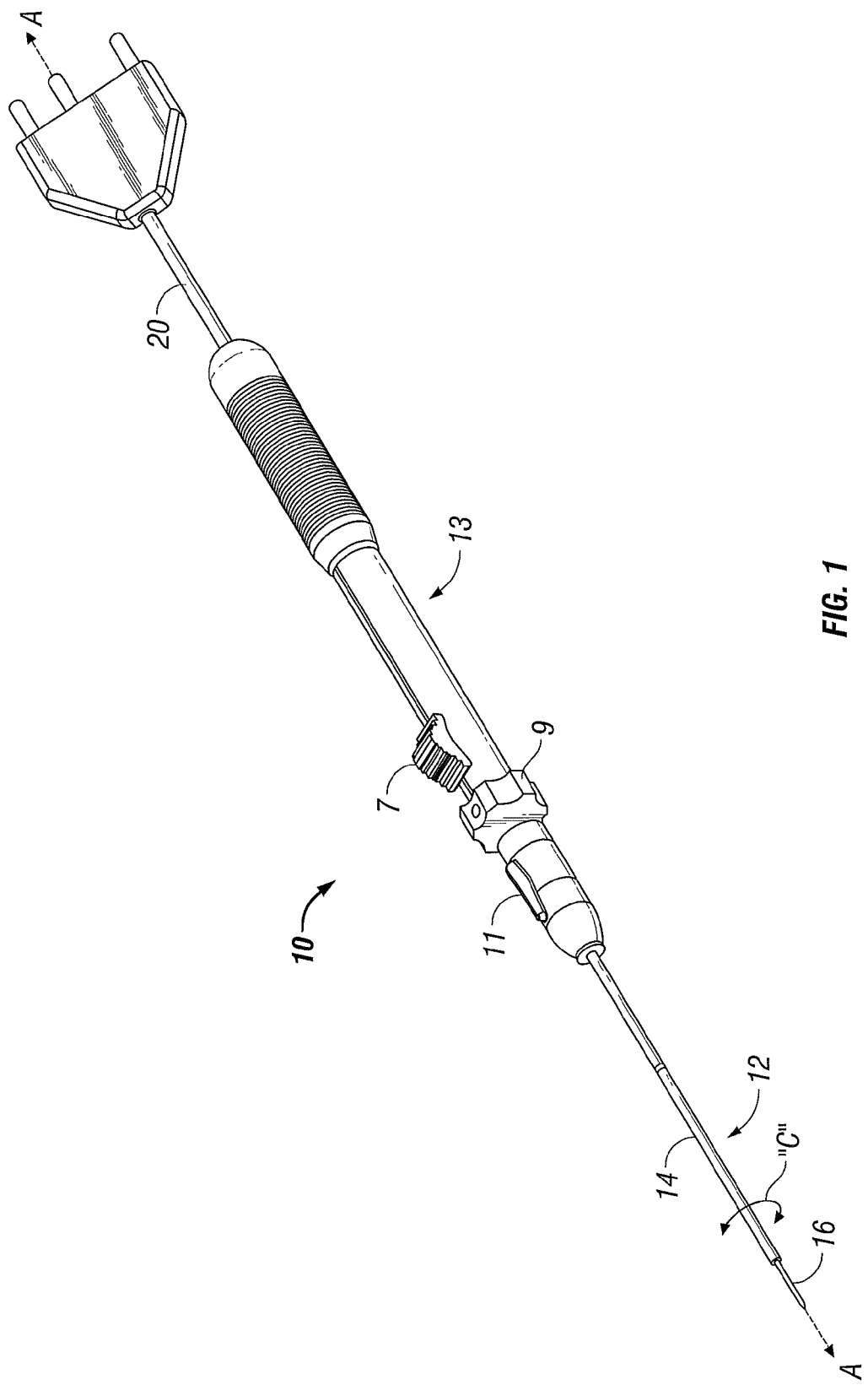
FIG. 1 is a perspective view of a microwave ablation device in accordance with an embodiment of the present disclosure.

Embodiments of the presently disclosed ablation devices are described in detail with reference to the drawings, in which like reference numerals designate identical or corresponding elements in each of the several views. As used herein the term "distal" refers to that portion of the ablation device, or component thereof, farther from the user while the term "proximal" refers to that portion of the ablation device or component thereof, closer to the user.

An energy applicator or ablation device (e.g., a microwave ablation device) in accordance with the present disclosure is referred to in the figures as reference numeral 10. While a microwave ablation device is described herein, it is contemplated that the present disclosure may also be used in connection with other types of ablation devices such as radiofrequency (RF), laser, ultrasound, cryotherapy, etc. Such ablation devices may include an antenna and/or an electrode.

Figure 2:
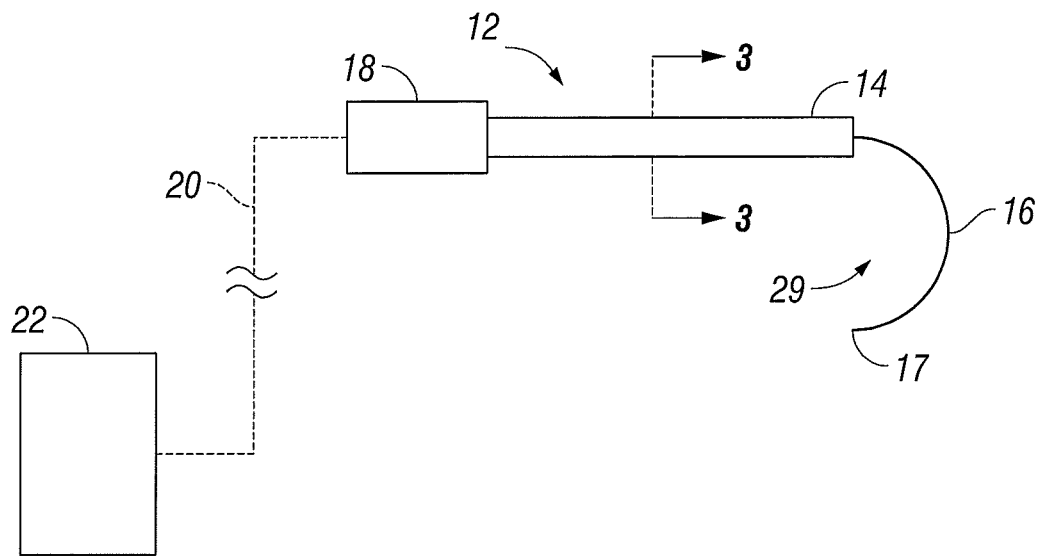
FIG. 2 is a schematic view of the microwave ablation device of FIG. 1 connected to a generator.

Referring initially to FIGS. 1 and 2, microwave ablation device 10 includes an antenna 12 and a handle portion 13. Antenna 12 includes a shaft 14 having an inner conductor 16 and an outer conductor 24. A cord 20 is shown to couple microwave ablation device 10 to an electrosurgical generator 22, for instance. In the disclosed embodiments, electrosurgical generator 22 includes at least one of an RF generator and a microwave (MW) generator and may include other modalities including ultrasound and optical, for instance. Additionally, an actuation element 7, a rotation knob 9 and an articulation knob 11 are illustrated in FIG. 1 in accordance with various embodiments of the present disclosure.

As seen in FIG. 2, inner conductor 16 may be extendable from outer conductor 24 to define an ablation region 29. Several types of inner conductors 16 may be used in connection with the disclosed microwave ablation device 10, including an inner conductor 16 configured to deploy substantially in line with outer conductor 24 (e.g., FIG. 1) and an inner conductor 16 configured to deploy in a curved orientation (e.g., FIGS. 2 and 5) along a curvilinear path. In the embodiment illustrated in FIG. 2, a proximal end of shaft 14 includes a coupler 18 that electrically couples antenna 12 to generator 22 via power transmission cord 20.

Figure 3:
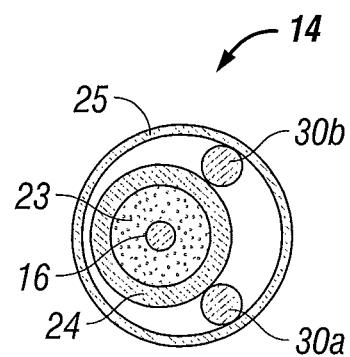
FIG. 3 is a cross-sectional view of a portion of a shaft of the microwave ablation device of FIGS. 1 and 2, as taken through 3-3 of FIG. 2.
Figure 4:
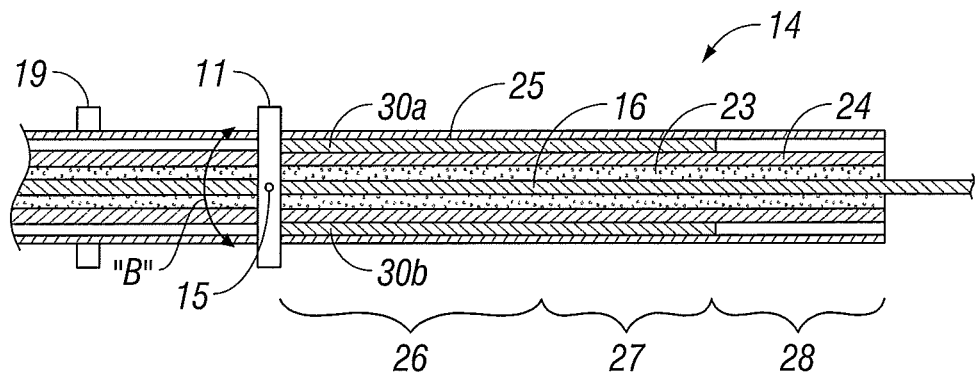
FIG. 4 is a longitudinal, cross-sectional, plan view of the shaft of the microwave ablation device of FIGS. 1-3, in accordance with an embodiment of the present disclosure.
Figure 5:
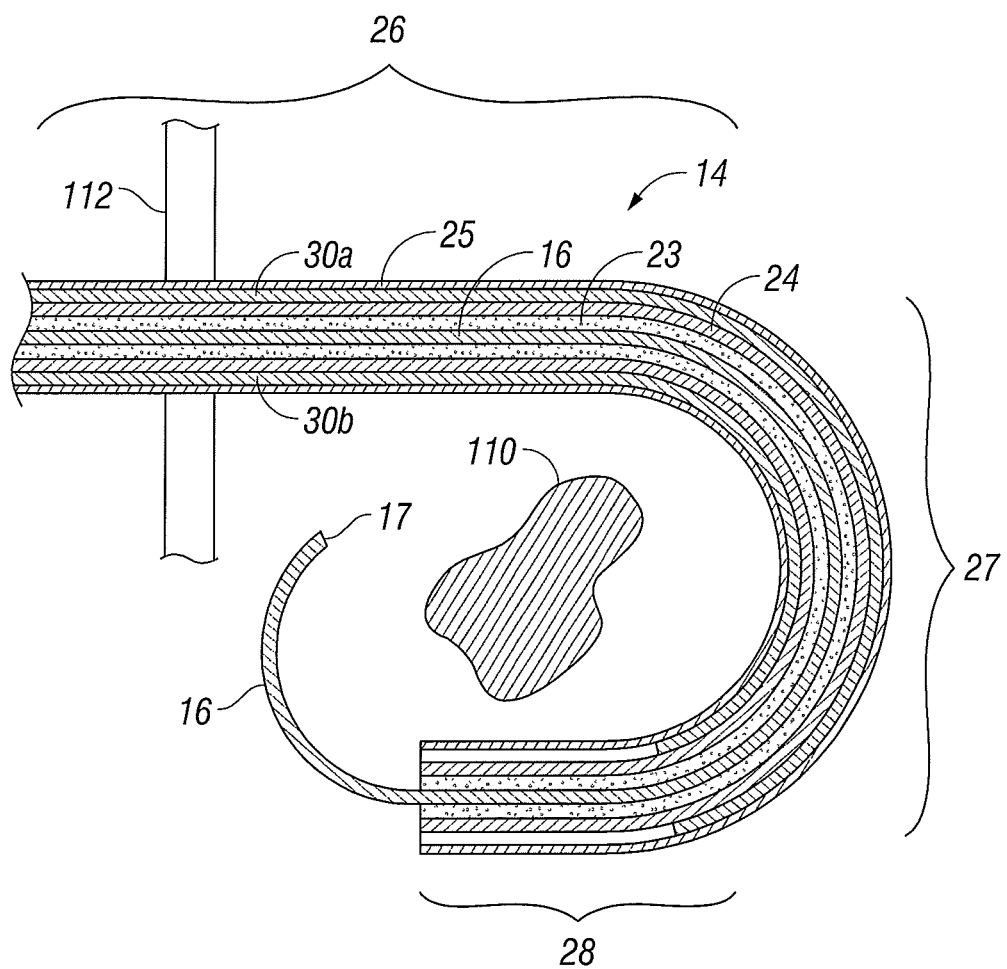
FIG. 5 is a longitudinal, cross-sectional view of a distal portion of the microwave ablation device of FIGS. 1-4 at least partially surrounding a treatment area.

With reference to FIGS. 3, 4 and 5, shaft 14 of antenna 12 includes a dielectric material 23 surrounding at least a portion of a length of inner conductor 16, and outer conductor 24 surrounding at least a portion of a length of dielectric material 23 and/or inner conductor 16. A pair of cables 30a, 30b extends adjacent outer conductor 24 of shaft 14. Additionally, an outer sheath 25 surrounds at least a portion of shaft 14 and cables 30a, 30b. Each cable 30a, 30b extends distally from handle portion 13 to an intermediate portion 27 of shaft 14. While FIG. 3 illustrates cables 30a and 30b at a specific location within shaft 14, cables 30a and 30b may be disposed at other positions between outer conductor 24 and outer sheath 25.

As seen in FIG. 4, a proximal end of each cable 30a and 30b is coupled to opposed sides of articulation knob 11 and a distal end of each cable 30a, 30b is coupled to intermediate portion 27 of shaft 14. In a disclosed embodiment, a proximal portion 26 of shaft 14 may be made of a semi-rigid material, intermediate portion 27 of shaft 14 (e.g., inner conductor 16, outer conductor 24 and/or dielectric material 23) may be made of a flexible material, and a distal portion 28 of shaft 14 may be made of a semi-rigid material. Such a configuration allows shaft 14 to articulate, bend or flex at intermediate portion 27, e.g., to facilitate access to various areas. Any suitable materials may be used, such as those that enable shaft 14 to be used for arthroscopic applications, for instance. In some embodiments, both proximal portion 26 and distal portion 28 may be flexible to facilitate delivery through a flexible endoscope, for example.

As seen in FIGS. 4 and 5, in use, upon distal movement of first cable 30a (and/or proximal movement of second cable 30b), intermediate portion 27 of shaft 14 moves or is articulated towards the right (or in a downward direction as viewed in FIG. 5). Similarly and/or concomitantly, in use, upon distal movement of second cable 30b (and/or proximal movement of first cable 30a), intermediate portion 27 of shaft 14 moves or is articulated towards the left or an opposite direction. In so doing, shaft 14 moves from a first position, where distal portion 28 of shaft 14 is substantially aligned with a longitudinal axis A-A (see FIG. 1) defined by handle portion 13, to at least a second position where distal portion 28 of shaft 14 is disposed at an angle relative to longitudinal axis A-A.

At least a portion of cables 30a, 30b are made of a suitable flexible and/or non-extendable/compressible material, allowing shaft 14 to be articulated along a curvilinear path and/or to be introduced through a scope (e.g., bronchoscope, colonoscope, etc.). Each cable 30a, 30b is made of a suitable non-conductive material. While a pair of cables 30a, 30b is shown in various figures herein, microwave ablation device 10 may include a single cable 30 for articulating shaft 14 in a single direction. Alternatively, microwave ablation device 10 may include more than two cables (e.g., four cables) for articulating shaft 14.

As seen in FIGS. 1 and 4, an example of a suitable articulation knob 11 is shown, for use in moving cables 30a, 30b, and thus for articulating shaft 14. As described above, a proximal end of each cable 30a, 30b is connected to or otherwise operatively secured to opposed sides of articulation knob 11. Accordingly, in use, as articulation knob 11 is rotated or pivoted about pivot 15 (as indicated by arrows "B"), cables 30a, 30b are caused to be translated distally or proximally, thus resulting in a desired direction of articulation of intermediate portion 27 of shaft 14, and thus a desired articulation and/or path of distal tip 17 of inner conductor 16. The amount of rotation of articulation knob 11 and thus axial translation of a particular cable 30a, 30b may correspond to an amount of articulation of shaft 14. In this manner, a profile of inner conductor 16 may be manipulated toward a desired treatment site (e.g., tumor 110 in FIG. 5) or to substantially surround the treatment site, for instance. In lieu of articulation knob 11, each cable 30a and 30b may be independently translatable, e.g., via a pair of articulation knobs, joysticks or slides supported on handle portion 13. Alternatively, the movement of cables 30a, 30b may be controlled electronically and/or remotely in any suitable manner.

Referring back to FIG. 1, actuation element 7 is shown disposed in mechanical cooperation with handle portion 13 and coupled (not shown) to inner conductor 16. As can be appreciated, distal and proximal translation of actuation element 7 with respect to handle portion 13 causes corresponding translation of inner conductor 16 for deployment from and/or retraction into shaft 14. Further, inner conductor 16 may be translatable with respect to outer conductor 24 and dielectric material 23.

In a disclosed embodiment, the connection between actuation element 7 and inner conductor 16 also enables rotation of shaft 14 (as indicated by arrow "C" of FIG. 1) with respect to handle portion 13, e.g., via rotation knob 9.

In accordance with an embodiment of the present disclosure, the connection between rotation knob 9 and shaft 14 allows shaft 14 to be rotated substantially about longitudinal axis A-A. Additionally, and with reference to FIGS. 1 and 4, rotation of shaft 14 and articulation of shaft 14 may be controlled independently.

As can be appreciated, the combination of the rotational and the articulation capabilities of device 10 allows shaft 14 and distal tip 17 of inner conductor 16 to be positioned at a multitude of positions adjacent and/or at least partially surrounding a desired tissue region. Accordingly, microwave ablation device 10 provides a great deal of versatility during laparoscopic, endoscopic, endoluminal, and transluminal procedures. As mentioned previously, device 10 may be capable of delivering any suitable energy, such as radiofrequency (RF), microwave (MW), laser, ultrasound and cryotherapy energy. In some embodiments, the ablative properties of device 10 may be enhanced by delivery of fluids (e.g., alcohol or chemotherapeutic agents, etc.) to the treatment site.

Microwave ablation device 10 may be introduced to the treatment site via a straight, arcuate, non-deployable and/or deployable applicator and/or introducer.

Conductors 16 and 24 may be made of a suitable conductive metal that may be semi-rigid or flexible, such as, for example, copper, gold, or other conductive metals with similar conductivity values. Alternatively, portions of conductors 16 and 24 may also be made from stainless steel, which may additionally be plated with other materials, e.g., other conductive materials, to improve their properties, e.g., to improve conductivity or decrease energy loss, etc.

For example, an inner conductor 16 made of stainless steel may have an impedance of about 50Ω. In order to improve a conductivity of stainless steel inner conductor 16, inner conductor 16 may be coated with a layer of a conductive material such as copper or gold. Although stainless steel may not offer the same conductivity as other metals, it does offer increased strength that is helpful to puncture tissue and/or skin 112 (FIG. 5).

Dielectric material 23, interposed between inner and outer conductors 16, 24, respectively, provides insulation therebetween and may be comprised of any suitable variety of conventional dielectric and/or insulative material.

Figure 6:
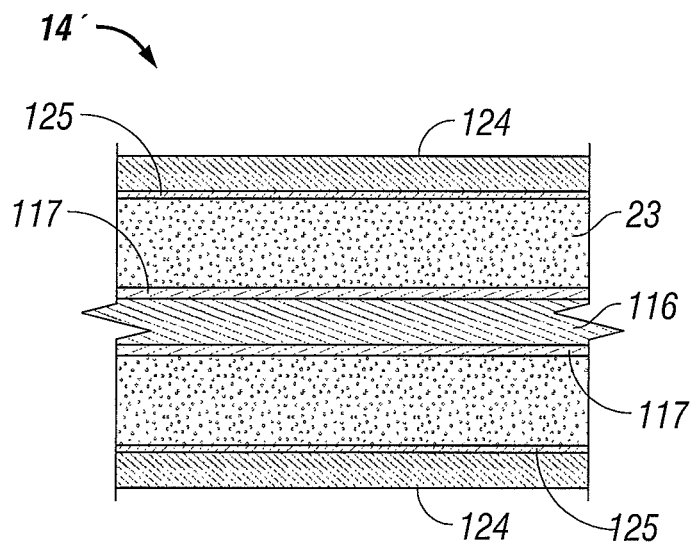
FIGS. 6 and 7 are longitudinal and transverse cross-sectional views, respectively, of a variation of the feedline of the microwave ablation device of FIG. 3 having plated conductive layers.
Figure 7:
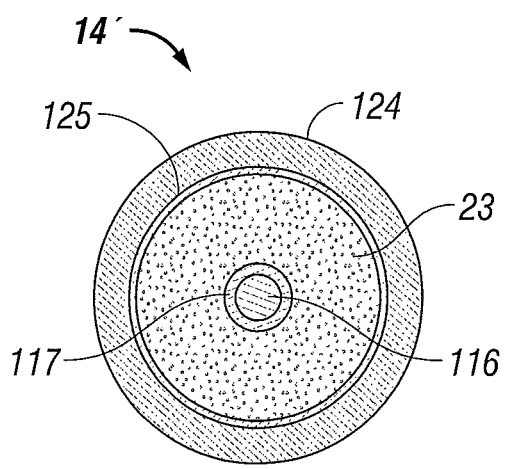

FIGS. 6 and 7 show longitudinal and transverse cross-sectional views, respectively, of a variation of a shaft 14' having conductive layers plated onto surfaces thereof to increase energy transmission and the like, according to an embodiment of the present disclosure. As shown, the outer surface of inner conductor 116 may be plated with a layer 117 of at least one additional conductive material, as described above. Likewise, the inner surface of outer conductor 124 may be similarly plated with a layer 125, that may be made of the same, similar, or different conductive material as layer 117. The addition of conductive layers 117 and/or 125 may increase energy transmission, aid in decreasing cable losses, in decreasing cable heating, and in distributing the overall temperature within the cable.

A method of treating tissue, using ablation device 10, is also included by the present disclosure. The method may include at least providing ablation device 10, such as described above, and moving at least one of cables 30a, 30b such that distal portion 28 of shaft 14 is substantially aligned with longitudinal axis A-A, to at least a second position where distal portion 28 of shaft 14 is disposed at an angle relative to longitudinal axis A-A.

An ablation system for ablating tissue is also included by the present disclosure. The ablation system includes an ablation device 10, such as described above, where an intermediate portion of antenna 12 (or other suitable energy applicator, such as an electrode) is movable from a first position where the distal tip of antenna 12 is substantially aligned with the longitudinal axis to at least a second position where the distal tip of antenna 12 is disposed at an angle to the longitudinal axis.

Various modifications may be made to the embodiments disclosed herein. Therefore, the above description should not be construed as limiting, but merely as exemplifications of various embodiments. Those skilled in the art will envision other modifications within the scope and spirit of the claims appended hereto.

The invention claimed is:

1. A flexible ablation device, comprising:
a handle portion;
a shaft extending distally from the handle portion, the shaft including:
an inner conductor including a length and a distal tip; and
an outer conductor substantially surrounding the inner conductor at least partially along the length thereof and defining a longitudinal axis, wherein at least a portion of the shaft is flexible and the inner conductor is axially translatable with respect to the outer conductor such that at least the distal tip of the inner conductor is positionable distally beyond a distal-most end of the outer conductor; and
at least one cable extending from the handle portion along at least a portion of a length of the shaft and configured to allow the shaft to be articulatable along a curvilinear path, wherein at least a portion of the at least one cable is flexible.

2. The flexible ablation device according to claim 1, further including at least a second cable extending from the handle portion along at least a portion of a length of the shaft, wherein, in response to movement of the second cable relative to the shaft, the distal tip of the outer conductor is movable from a first position to a second position.

3. The flexible ablation device according to claim 2, wherein the first cable and the second cable are independently moveable relative to one another.

4. The flexible ablation device according to claim 2, further including an articulation knob disposed on the handle portion, and wherein a proximal portion of the first cable is operably connected to the articulation knob and a proximal portion of the second cable is operably connected to the articulation knob, wherein movement of the articulation knob causes at least one of first and second cables to move.

5. The flexible ablation device according to claim 1, wherein the shaft is rotatable with respect to the handle portion along the longitudinal axis.

6. The flexible ablation device according to claim 1, wherein the distal tip of the inner conductor is movable along a curvilinear path.

7. The flexible ablation device according to claim 1, wherein at least a portion of the inner conductor is advanceable substantially along the longitudinal axis with respect to the outer conductor.

8. The flexible ablation device according to claim 1, wherein, in response to movement of the at least one cable relative to the handle portion, a distal tip of the outer conductor is movable from a first position wherein the distal tip is substantially aligned with the longitudinal axis to at least a second position wherein the distal tip is disposed at an angle relative to the longitudinal axis.

9. The flexible ablation device according to claim 1, further including an articulation knob disposed on the handle portion, and wherein a proximal portion of the at least one cable is operably connected to the articulation knob, wherein movement of the articulation knob causes corresponding movement of the at least one cable.

10. A method of treating tissue, comprising:
providing a flexible ablation device, including:
an antenna including:
an inner conductor including a length;
an outer conductor substantially surrounding the inner conductor at least partially along the length thereof and defining a longitudinal axis,
wherein at least a portion of the antenna is made of a flexible material; and
at least one cable extending along a portion of the antenna, wherein at least a portion of the at least one cable is flexible;
introducing the antenna such that at least a distal tip of the inner conductor is adjacent a target site;
moving the at least one cable such that a distal tip of the outer conductor moves from a first position wherein the distal tip is substantially aligned with the longitudinal axis to at least a second position wherein the distal tip is disposed at an angle relative to the longitudinal axis; and
axially translating at least a portion of the inner conductor with respect to the outer conductor such that at least the distal tip of the inner conductor is positioned distally beyond a distal-most end of the outer conductor.

11. The method of claim 10, wherein the antenna is a coaxial cable.

12. The method of claim 10, further including rotating the antenna about the longitudinal axis.

13. The method of claim 10, further including providing a second cable operably connected adjacent the portion of the antenna made of a flexible material.

14. The method of claim 10, further including moving the distal tip of the inner conductor along a curvilinear path.

* * * * *